(12) United States Patent
Salm et al.

(10) Patent No.: US 10,709,747 B2
(45) Date of Patent: Jul. 14, 2020

(54) ENCAPSULATED CANNABINOID FORMULATIONS FOR ORAL DELIVERY

(71) Applicant: Nutrae, LLC, Sarasota, FL (US)

(72) Inventors: Jacqueline L. Salm, Tampa, FL (US); Christopher G. Witowski, Tampa, FL (US)

(73) Assignee: NUTRAE, LLC, Sarasota, FL (US)

( * ) Notice: Subject to any disclaimer, the term of this patent is extended or adjusted under 35 U.S.C. 154(b) by 0 days.

(21) Appl. No.: 16/246,400

(22) Filed: Jan. 11, 2019

(65) Prior Publication Data

US 2019/0216869 A1     Jul. 18, 2019

Related U.S. Application Data

(60) Provisional application No. 62/617,003, filed on Jan. 12, 2018.

(51) Int. Cl.

| | | |
|---|---|---|
| *A61K 36/00* | (2006.01) | |
| *A61K 36/185* | (2006.01) | |
| *A61K 9/00* | (2006.01) | |
| *A61K 45/06* | (2006.01) | |
| *A61K 31/352* | (2006.01) | |
| *A23L 33/105* | (2016.01) | |
| *A23L 2/56* | (2006.01) | |
| *A61K 9/107* | (2006.01) | |
| *A61K 47/10* | (2017.01) | |
| *A61K 9/70* | (2006.01) | |
| *A61K 31/05* | (2006.01) | |
| *A61K 31/192* | (2006.01) | |

(52) U.S. Cl.
CPC .............. *A61K 36/185* (2013.01); *A23L 2/56* (2013.01); *A23L 33/105* (2016.08); *A61K 9/006* (2013.01); *A61K 9/0014* (2013.01); *A61K 9/0019* (2013.01); *A61K 9/0073* (2013.01); *A61K 9/1075* (2013.01); *A61K 9/7084* (2013.01); *A61K 31/352* (2013.01); *A61K 45/06* (2013.01); *A61K 47/10* (2013.01); *A23V 2002/00* (2013.01); *A23V 2200/242* (2013.01); *A23V 2250/2132* (2013.01); *A61K 31/05* (2013.01); *A61K 31/192* (2013.01)

(58) Field of Classification Search
None
See application file for complete search history.

(56) References Cited

U.S. PATENT DOCUMENTS

| | | |
|---|---|---|
| 2005/0266061 A1 | 12/2005 | Stinchcomb et al. |
| 2014/0357708 A1 | 12/2014 | Murty et al. |
| 2015/0126595 A1 | 5/2015 | Smith |
| 2016/0303039 A1 | 10/2016 | Smith et al. |
| 2017/0043932 A1* | 2/2017 | Byun ..................... A61K 31/05 |
| 2019/0060225 A1* | 2/2019 | Mandel ............... A61K 9/0056 |
| 2019/0192428 A1* | 6/2019 | Goskonda ........... A61K 31/352 |

FOREIGN PATENT DOCUMENTS

| | | |
|---|---|---|
| AU | 2013213706 B2 | 8/2013 |
| WO | 200103668 A1 | 1/2001 |
| WO | 2002064109 A2 | 8/2002 |
| WO | 2012033478 A1 | 3/2012 |
| WO | 2015161165 A1 | 10/2015 |
| WO | 2015200049 A1 | 12/2015 |
| WO | 2016147186 A1 | 9/2016 |

OTHER PUBLICATIONS

Officer Jose Ruiz Fernandez; International Search Report and Written Opinion; PCT/US2019/013376; dated Mar. 29, 2019; 12 pages.
Officer Jose Ruiz Fernandez; International Search Report and Written Opinion; PCT/US2019/013374; dated Mar. 29, 2019; 23 pages.
Officer Anita Meacle; International Search Report and Written Opinion; PCT/US2019/013374; dated Apr. 5, 2019; 12 pages.

* cited by examiner

*Primary Examiner* — Michael Barker
(74) *Attorney, Agent, or Firm* — Dickinson Wright PLLC; Kristopher Lance Anderson (57) ABSTRACT

Preparation of cannabinoid formulations containing: Δ9-tetrahydrocannabinol (Δ9-THC), Δ8-tetrahydrocannabinol (Δ8-THC), Δ9-tetrahydrocannabinolic acid (THCa), cannabidiol (CBD), cannabidiolic acid (CBDa), cannabigerol (CBG), cannabichromene (CBC) and cannabinol (CBN), either alone or in combinations henceforth known as *Cannabis*, have been created using an emulsification process to encapsulate cannabinoids. The aqueous-based method involves micellular encapsulation of cannabinoids, a method that has been used to increase the bioavailability of poorly permeable, lipophilic drugs. These preparations demonstrates the viability of sublingual, buccal, or oral delivery using an aqueous-based encapsulation method, including as a beverage or drink.

19 Claims, 4 Drawing Sheets

ENCAPSULATED CANNABINOID FORMULATIONS FOR ORAL DELIVERY

CROSS-REFERENCE TO RELATED APPLICATIONS

This application claims priority to U.S. Provisional Patent Application Ser. No. 62/617,003, filed on Jan. 12, 2018, entitled "ENCAPSULATED CANNABINOID FORMULATIONS" of which is hereby incorporated herein by reference in their entirety for all purposes.

This application includes material that is subject to copyright protection. The copyright owner has no objection to the facsimile reproduction by anyone of the patent disclosure, as it appears in the Patent and Trademark Office files or records, but otherwise reserves all copyright rights whatsoever.

FIELD

The present invention relates in general to the field of drug delivery formulations. In particular, the present invention provides for the encapsulation of poorly soluble cannabinoids for efficient delivery to a subject.

BACKGROUND

*Cannabis* is an annual, primarily dioecious, flowering herb. The genera *Cannabis* is considered to be monospecific (*Cannabis sativa* L.) which is divided into several subspecies (*C. sativa* subsp. *sativa, C. sativa* subsp. *indica, C. sativa* subsp. *ruderalis, C. sativa* subsp. *spontanea, C. sativa* subsp. *kafiristanca*). However, the chemical and morphological distinctions by which *Cannabis* has been split into these subspecies are often not readily discernible, appear to be environmentally modifiable, and vary in a continuous fashion. For most purposes, it will suffice to apply the name *Cannabis sativa* to all *Cannabis* plants encountered.

Cannabinoids are chemical compounds found in the *Cannabis* plant that interact with receptors in the brain and body to create various effects. *Cannabis* contains over 400 compounds including over 100 cannabinoids, which are aryl-substituted meroterpenes unique to the plant genus *Cannabis*. The pharmacology of most of the cannabinoids is largely unknown but the most potent psychoactive agent, $\Delta^9$-tetrahydrocannabinol ($\Delta^9$-THC, or THC), has been isolated, synthesized and much studied due to its abundance and psychoactive attributes. Other plant-based cannabinoids include $\Delta^9$-tetrahydrocannabinolic acid, $\Delta^8$-THC, cannabigerol, cannabidiolic acid, and cannabidiol (CBD). These and other cannabinoids have additive, synergistic or antagonistic effects with THC and may modify its actions when *Cannabis* products are consumed.

Cannabinoid containing extracts can be produced from a wide variety of methods (sub/supercritical $CO_2$, hydrocarbons, alcohols, and by heated/pressurized means) and can be further purified using winterization (precipitation) in alcohols, distillation, or chromatographic separation. The resulting cannabinoids are highly lipophilic with Log P values ranging from 5 to 9, making them practically insoluble in water. These properties are not conducive to traditional pharmaceutical drug delivery methods, which is why smoking is still a preferred method for *Cannabis* consumption.

It is well known in cosmeceutical and pharmaceutical preparations that above the critical micelle concentration of one or more surfactants that micelles will be formed during emulsification. The micelles can take many shapes (spherical, cylinders, or other arrangements), structures (unilamellar or multilamellar), and names (liposomes, niosomes, and ethosomes among others). Various reports have concluded that these micelles can also be used to encapsulate active ingredients for delivery of pharmaceuticals (Hung et al. 2001; Narang et al. 2007; Kwon, 2012) as well as increase the bioavailability of drugs with poor water solubility (Keller et al. 1999; Touitou et al. 2000; O'Driscoll et al. 2008).

Despite efforts to create highly soluble and bioavailable cannabinoid formulations, there remains a need in the art for cannabinoid formulations that have increased bioavailability and which are conducive to use with traditional drug delivery methods.

SUMMARY OF THE DISCLOSURE

It is therefore an object of the present invention to provide water-soluble cannabinoid formulations that are surfactant-stabilized and that have increased bioavailability.

In one aspect of the present invention, various preparations are presented to produce an oil-in-water emulsion in which the hydrophilic-lipophilic balance (HLB) is optimized to produce a stable emulsion. A blend of surfactants can increase the stability of emulsions and create self-emulsifying drug delivery systems (SEDDS). During emulsification, micelles are created which have the ability to capture cannabinoids and other *Cannabis*-based ingredients within the hydrophobic inner core. The encapsulation protects labile ingredients and the hydrophilic heads of the micellular outer shell increase drug delivery capabilities.

In one aspect of the present invention, a cannabinoid composition is provided, said composition comprising: a cannabinoid preparation; at least one surfactant; at least one co-solvent; and water; wherein said cannabinoid composition yields the cannabinoid preparation capable of having increased bioavailability. In another aspect, the at least one surfactant comprises at least two surfactants. Further, the surfactants have an HLB in the range of 1 to 8 and form a self-assembling emulsion. In another aspect, the at least one surfactant comprises an HLB in the range of 9-20. In yet another aspect, the at least one surfactant is selected from a group consisting of: oleic acid, sunflower oil, lecithin, phosphatidylcholine, isopropyl myristate, stearic acid, medium and long chain triglycerides, Labrasol, polysorbate 20, polysorbate 80, or other ethoxylated surfactant, and sorbitan trioleate, other sorbitan surfactant, and combinations thereof.

In another aspect of the present invention, the at least one co-solvent is selected from a group consisting of: methanol, ethanol, isopropyl alcohol, butanol, pentanol, hexanol, ethylene glycol, propylene glycol, dipropylene glycol, glycerol, glycerin, erythritol, xylitol, mannitol, sorbitol, diethylene glycol monoethyl ether (Transcutol), any derivative thereof, and combinations relating thereto.

In one aspect cannabinoid preparation of the present invention is encapsulated by surfactants to form micelles having uni-, bi-, or multi-lamellar structures.

In another aspect, the composition of the present invention comprises a stabilizer in the range of 0.01% to 3% (w/w). In yet another aspect, the composition comprises a thickening agent in the range of 0.01% to 5% (w/w). In another aspect, the composition comprises terpenes in the range of 0.1% to 5% (w/w). In another aspect, the total cannabinoid preparation of the present invention ranges from 0.001% to 40% (w/w), the at least one surfactants range from 2% to 50% (w/w), the at least one co-solvents range from 5% to 70% (w/w), the water ranges from 2% to 55% (w/w), and the stabilizer ranges from 0.01% to 3% (w/w).

It is a further object of the present invention to provide a cannabinoid composition, said composition comprising a cannabinoid preparation, at least one surfactant, at least one co-solvent; and water; wherein said cannabinoid composition yields the cannabinoid preparation capable of having increased bioavailability. In one aspect the at least one surfactant comprises at least two surfactants. In another aspect, the two surfactants comprise an HLB in the range of 1 to 8 and form a self-assembling emulsion. In even another aspect, the at least one surfactant comprises an HLB in the range of 9-20. The at least one surfactant may therefore be selected from a group consisting of: oleic acid, sunflower oil, lecithin, phosphatidylcholine, isopropyl myristate, stearic acid, medium and long chain triglycerides, Labrasol, polysorbate 20, polysorbate 80, or other ethoxylated surfactant, and sorbitan trioleate, or other sorbitan surfactant.

In one aspect the at least one co-solvent is selected from a group consisting of: methanol, ethanol, isopropyl alcohol, butanol, pentanol, hexanol, ethylene glycol, propylene glycol, dipropylene glycol, glycerol, glycerin, erythritol, xylitol, mannitol, sorbitol, diethylene glycol monoethyl ether (Transcutol), any derivative thereof, and combinations relating thereto.

It is therefore an object of the present invention to provide a cannabinoid composition for oral delivery, said composition comprising: a cannabinoid preparation ranging from 0.001% to 3% (w/w); at least one surfactant ranging from 2% to 15% (w/w); at least one co-solvent ranging from 20% to 65% (w/w); at least one flavoring composition ranging from 0.1% to 5% (w/w); a preservative ranging from 0.01% to 5% (w/w); and water ranging from 2% to 77% (w/w); wherein said composition yields the cannabinoid preparation capable of having increased bioavailability and operable for oral delivery.

It is another object of the present invention to provide a cannabinoid composition for consumption as a beverage, said composition comprising: a first measured amount of a cannabinoid-containing suspension comprising: a cannabinoid preparation ranging from 0.001% to 3% (w/w); at least one surfactant ranging from 2% to 15% (w/w); at least one co-solvent ranging from 20% to 65% (w/w); at least one flavoring composition ranging from 0.1% to 5% (w/w); a preservative ranging from 0.01% to 5% (w/w); and water ranging from 2% to 99.9% (w/w); and a liquid composition; wherein said cannabinoid composition yields the cannabinoid-containing suspension preparation capable of having increased bioavailability when consumed as a beverage.

In one aspect, the cannabinoid compositions are capable of oral, sublingual or buccal delivery. In another aspect the at least one surfactant comprises two or more surfactants. In another aspect the two or more surfactants comprise an HLB in the range of 1 to 8 and form a self-assembling emulsion. In another aspect, the at least one surfactant comprises an HLB in the range of 9-20.

In another aspect, the at least one surfactant may include, but is not limited to: oleic acid, sunflower oil, lecithin, phosphatidylcholine, isopropyl myristate, stearic acid, medium and long chain triglycerides, Labrasol, polysorbate 20, polysorbate 80, or other ethoxylated surfactant, and sorbitan trioleate, or other sorbitan surfactant.

In another aspect, the at least one co-solvent may include, but is not limited to: methanol, ethanol, isopropyl alcohol, butanol, pentanol, hexanol, ethylene glycol, propylene glycol, dipropylene glycol, glycerol, glycerin, erythritol, xylitol, mannitol, sorbitol, diethylene glycol monoethyl ether (Transcutol), any derivative thereof, and combinations relating thereto.

The cannabinoid preparation may be encapsulated by surfactants to form micelles having uni-, bi-, or multi-lamellar structures. In another aspect, the cannabinoid composition further comprises a stabilizer in the range of 0.01% to 3% (w/w). In another aspect, the cannabinoid composition further comprises a thickening agent in the range of 0.01% to 10% (w/w). In another aspect, the cannabinoid composition further comprises terpenes in the range of 0.1% to 5% (w/w).

In another aspect, the present invention provides a method for preparing a cannabinoid composition having increased bioavailability, the method comprising forming a cannabinoid composition comprising: preparing an oil phase composition comprising: a cannabinoid preparation; at least one surfactant; and at least one co-solvent; preparing a water phase composition comprising water; at least one co-solvent; and a stabilizing agent effectively mixing the oil phase composition and the water phase composition, which may include under high shear conditions, to form micelles within a microemulsion; centrifugation to purify micelles and/or further create micelles and; introducing a second water phase composition comprising: water; and a stabilizing agent; wherein said cannabinoid composition yields the cannabinoid preparation capable of having increased bioavailability.

In yet another aspect, the present invention provides a method for preparing a cannabinoid composition having increased bioavailability, the method comprising forming a cannabinoid composition comprising: preparing an oil phase composition comprising: a cannabinoid preparation; at least one surfactant; and at least one co-solvent; preparing a water phase composition comprising water; at least one co-solvent; and a stabilizing agent; mixing the oil phase composition and the water phase composition to form micelles within a microemulsion; and introducing a second water phase composition comprising: water; and a stabilizing agent; wherein said cannabinoid composition yields the cannabinoid preparation capable of having increased bioavailability.

It is another object of the present invention to provide a method for treating a subject, comprising: orally administering a cannabinoid composition into the subject at least once per day in a dose amount effective to treat the subject's symptoms; wherein the oral cannabinoid composition comprises: an oil phase composition comprising: a cannabinoid preparation; at least one surfactant; and at least one co-solvent; a water phase composition comprising water; at least one co-solvent; and a stabilizing agent; wherein the oil phase composition and the water phase composition are mixed to form micelles within a microemulsion; introducing a second water phase composition comprising: water; and a stabilizing agent; wherein said cannabinoid composition yields the cannabinoid preparation capable of having increased bioavailability when orally administered.

For any methods set forth in the present invention, the at least one surfactant comprises an HLB in the range of 1 to 8 and forms a self-assembling emulsion with the at least one surfactant described above. In another aspect, the method described herein may further comprise the step of sonicating the microemulsion to increase the micelles and decrease the particle size of said micelles.

It therefore an object of the present invention to provide a method for preparing a cannabinoid composition having increased bioavailability, the method comprising forming a cannabinoid composition comprising: preparing an oil phase composition comprising, a cannabinoid preparation, at least one surfactant; and at least one co-solvent, preparing a water phase composition comprising water and a stabilizing agent, mixing the oil phase composition and the water phase composition to form micelles within a microemulsion, sonicating the microemulsion to increase the micelles and decrease the particle size of said micelles, centrifugation to purify micelles and/or further create micelles and introducing a second water phase composition comprising water and a stabilizing agent, wherein said cannabinoid composition yields the cannabinoid preparation capable of having increased bioavailability.

BRIEF DESCRIPTION OF THE DRAWINGS

The present invention is further described in the detailed description which follows, in reference to the noted plurality of drawings by way of non-limiting examples of exemplary embodiments, in which like reference numerals represent similar parts throughout the several views of the drawings, and wherein.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

While the making and using of various embodiments of the present invention are discussed in detail below, it should be appreciated that the present invention provides many applicable inventive concepts that can be embodied in a wide variety of specific contexts, goods, or services. The specific embodiments discussed herein are merely illustrative of specific ways to make and use the disclosure and do not delimit the scope of the disclosure.

All publications and patent applications mentioned in the specification are indicative of the level of skill of those skilled in the art to which this disclosure pertains. All publications and patent applications are herein incorporated by reference to the same extent as if each individual publication or patent application was specifically and individually indicated to be incorporated by reference.

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It will be understood that various changes may be made in the function and arrangement of elements without departing from the spirit and scope of the disclosure as set forth in the appended claims.

Specific details are given in the following description to provide a thorough understanding of the embodiments. However, it will be understood by one of ordinary skill in the art that the embodiments may be practiced without these specific details. For example, systems, processes, and other elements in the instant disclosure may be shown as components in block diagram form in order not to obscure the embodiments in unnecessary detail. In other instances, well-known processes, structures, and techniques may be shown without unnecessary detail in order to avoid obscuring the embodiments. Further, like reference numbers and designations in the various drawings indicated like elements.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context Also, it is noted that individual embodiments may be described as a process which is depicted as a flowchart, a flow diagram, or a block diagram. Although a flowchart may describe the operations as a sequential process, many of the operations can be performed in parallel or concurrently. In addition, the order of the operations may be re-arranged.

It has been shown that self-emulsifying drug delivery systems (SEDDS), which are isotropic mixtures of oils, surfactants, solvents and co-solvents/surfactants, can be used for the design of formulations in order to improve the oral absorption of highly lipophilic drug compounds. Although the exact mechanisms responsible for the enhanced absorption and bioavailability are not fully known, it is believed that various factors, including improved drug solubilization, act to increase the particle diffusion through membranes and/or at the point of absorption. The advantages of these systems include not only improved drug solubilization but also enhanced release and absorption properties due to the already dissolved form of the drug in the formulation and the resulting small droplet size, which provides a large interfacial surface area.

The efficiency of oral absorption of the drug compound from the SEDDS is dependent on many formulation-related parameters, including oil/surfactant ratios, surfactant concentration, polarity or hydrophobic-lipophilic balance of the resulting emulsion, droplet size and charge, the combination of which determines the self-emulsification ability. All of these factors must be designed to accommodate the desired drug, typically a single compound or salt derivative. As a result, only very specific pharmaceutical excipient combinations actually lead to efficient self-emulsifying systems. Although many studies have been carried out, there are few oral drug products on the pharmaceutical market formulated as SEDDS, confirming the difficulty of formulating hydrophobic drug compounds into such delivery systems.

Of even greater difficulty are the use of extracted oils such as *Cannabis* derived oils and related derivatives, including chemical substances related to tetrahydrocannabinol (THC) and its acid form THCa, cannabidiol (CBD) and its acid form CBDa, cannabinol (CBN), cannabigerol (CBG), tetrahydrocannabivarin (THCV), cannabichromene (CBC), and other substances that bind to cannabinoid receptors. Other known cannabinoids include tetrahydrocannabinol, $\Delta^8$-tetrahydrocannabinol, $\Delta^8$-tetrahydrocannabinol-DMH, $\Delta^9$-tetrahydrocannabinol propyl analogue (THCV), 11-hydroxy-tetrahydrocannabinol, 11-nor-9-carboxy-tetrahydrocannabinol, 5'-azido-$\Delta^8$-tetrahydrocannabinol, AMG-I, AMG-3, AM411, AM708, AM836, AM855, AM919, AM926, AM938, cannabidiol propyl analogue (CBDV), cannabichromene propyl analogue, cannabigerol, CP 47497, CP 55940, CP 55244, CP 50556, CT-3 (ajulemic acid), dimethylheptyl HHC, HU-210, HU-211, HU-308, WIN 55212-2, desacetyl-L-nantradol, dexanabinol, JWH-051, levonantradol, L-759633, nabilone, 0-1184, and mixtures thereof. In addition, terpenes present in extracted *Cannabis* oils provide additional desired qualities when effectively administered or incorporated into compositions of the present invention, including flavoring.

SEDDS systems are desired for use with cannabinoids for multiple reasons; first, due to the possibility of drug or formulation stability resulting from the SEDDS processing; or that the emulsifying system may result in too rapid of absorption and higher peak concentrations of the drug; and lastly, large concentrations of surfactant in the SEDDS system may cause gastrointestinal irritation. It is thus an embodiment of the present invention to develop a SEDDS for delivery of extracted *Cannabis*, focusing on factors critical to achieving enhanced or increased bioavailability, increased chemical and enzymatic stability, enhanced *Cannabis* derivative dissolution, higher interfacial absorption area, and enhanced permeation. While difficulties in optimizing SEDDS formulations traditionally require specific attention to the active pharmaceutical ingredient (API) characteristics, the present invention requires development of a SEDDS comprising entire extracted *Cannabis* oils or *Cannabis* preparations comprising multiple derivatives of *Cannabis*.

The present invention presents a novel aqueous self-emulsifying drug delivery system (SEDDS) *Cannabis* preparation capable of administration through various means, including but not limited to: oral delivery, sublingual delivery, buccal delivery, and other traditional gastrointestinal delivery means. In one embodiment, preparations involving *Cannabis* extracts are presented to produce an oil-in-water emulsion in which the hydrophilic-lipophilic balance (HLB) is optimized to produce a stable emulsion. A blend of surfactants can further increase the stability of emulsions and create self-emulsifying drug delivery systems (SEDDS).

Solvents such as alcohols [ethanol, isopropanol, propylene glycol, dipropylene glycol, diethylene glycol monoethyl ether (Transcutol), and glycerin] were screened for their solubility and stability in the formulation. These alcohols are known permeability enhancers and previous work (Touitou et al. 2000; Lodzki et al. 2003) has displayed higher encapsulation efficiency and greater micelle flexibility; resulting in higher intercellular permeability of lipophilic drugs including CBD. Surfactants are chosen in order to maintain a Hydrophilic-Lipophilic Balance (HLB) of 1-8, which also produce micelles that encapsulate *Cannabis* ingredients. The HLB of a surfactant is a measure of the degree to which it is hydrophilic or lipophilic, determined by calculating values for the different regions of the molecule. Using the methodology described by Griffin in 1949, surfactants may be described as follows:

$$HLB = 20 * M_h / M$$

where $M_h$ is the molecular mass of the hydrophilic portion of the molecule, and M is the molecular mass of the whole molecule, giving a result on a scale of 0 to 20. An HLB value of 0 corresponds to a completely lipophilic/hydrophobic molecule, and a value of 20 corresponds to a completely lipophobic/hydrophilic molecule. The HLB value can be used to predict the surfactant properties of a molecule:

| | |
|---|---|
| <10 | Lipid-soluble (water-insoluble) |
| >10 | Water-soluble (lipid-insoluble) |
| 1 to 3 | Anti-foaming agent |
| 3 to 8 | W/O (water in oil) emulsifier |
| 7 to 9 | Wetting and spreading agent |
| 13 to 16 | Detergent |
| 8 to 16 | O/W (oil in water) emulsifier |
| 16 to 18 | Solubilizer or hydrotrope |

Surfactants may include: sorbitan trioleate, polysorbate 80, polysorbate 20, isopropyl myristate, medium chain triglycerides, Labrasol, capric/caprylic glycerides, oleic acid, stearic acid, lecithin, and phosphatidylcholine. Other surfactants and oils include: polyethoxylated surfactants, PEG-modified surfactants, mineral oil, vegetable oils (sesame, corn, cottonseed, almond, pecan, peanut, sunflower, safflower, olive, and soybean), animal oils, castor and coconut oil. An exemplary oil-in-water emulsion will orientate the polar heads of the surfactants outward, producing uni- to multi-lamellar structures, to increase lipid membrane fluidity and can penetrate intercellularly through the skin by their small size (<200 nm). These properties apply to all biological lipid bilayer membranes including oral mucosal and gastrointestinal permeability and flux.

In another embodiment, a variety of polymers and thickening agents can be employed to further stabilize the emulsion and provide favorable drug release properties. Acrylate based polymers were screened for stability and drug release include Carbopol 980, Carbopol 5984, Ultrez 10, Pemulen TR-1, and Pemulen TR-2. These polymers are acidic in nature and need a base to neutralize the pH. Common bases include: sodium hydroxide, potassium hydroxide, triethanolamine, arginine, or other suitable base. Additionally, other thickening agents can be used including: hydroxyethyl cellulose, hydroxypropylmethyl cellulose, xanthan gum, locust bean gum, and saponin containing extracts (*Quillaja* spp., *Yucca* spp., *Glycyrrhiza* spp.).

For the purpose of the present invention, the term 'increased bioavailability' refers to the increase of a composition's presences at the site of action, and further may include the proportion of a drug or other substance which enters the circulation when introduced into the body and so is able to have an active effect. Increased bioavailability, when referenced, is generally representing a higher level of bioavailability compared to individual cannabinoid compositions or traditional oil phase compositions, as distinguished in FIG. 3.

In another embodiment, the compositions of the present invention are capable of being incorporated into numerous oral delivery types, such as solids, liquids, gels, and the like. For example, the compositions of the present invention may be added to ingredient mixes for beverages, such as juices, sports drinks, elixirs, or carbonated beverages, wherein the SEDDS are suspended within the liquid. Embodiments of the present invention make concentrated *Cannabis* oil emulsifiable and stable through mixing SEDDS within a liquid composition while the flavor can be adjusted from tasteless to any desired flavor using natural or synthetic flavoring agents. This composition is effective as a food and beverage additive and could have a wide range of CBD and/or THC levels or ratios, depending on the desired outcome and can provide users an option to decide the level of acceptable psychoactive effects caused mainly by THC, while getting the medical benefits of CBD.

In another embodiment of the present invention, the cannabinoid compositions are capable of oral, sublingual or buccal delivery. In another aspect the at least one surfactant comprises two or more surfactants. In another aspect the two or more surfactants comprise an HLB in the range of 1 to 8 and form a self-assembling emulsion. In another aspect, the at least one surfactant comprises an HLB in the range of 9-20.

In another embodiment, the at least one surfactant may include, but is not limited to: oleic acid, sunflower oil, lecithin, phosphatidylcholine, isopropyl myristate, stearic acid, medium and long chain triglycerides, Labrasol, polysorbate 20, polysorbate 80, or other ethoxylated surfactant, and sorbitan trioleate, or other sorbitan surfactant.

In another embodiment, the at least one co-solvent may include, but is not limited to: methanol, ethanol, isopropyl alcohol, butanol, pentanol, hexanol, ethylene glycol, propylene glycol, dipropylene glycol, glycerol, glycerin erythritol, xylitol, mannitol, sorbitol, diethylene glycol monoethyl ether (Transcutol), any derivative thereof, and combinations relating thereto.

The cannabinoid preparation may be encapsulated by surfactants to form micelles having uni-, bi-, or multi-lamellar structures. In another embodiment, the cannabinoid composition further comprises a stabilizer in the range of 0.01% to 3% (w/w). In another aspect, the cannabinoid composition further comprises a thickening agent in the range of 0.01% to 10% (w/w). In another aspect, the cannabinoid composition further comprises terpenes in the range of 0.1% to 5% (w/w).

It is yet another embodiment to provide an additional sonication step to the microemulsion formed. Ultrasonic shock or "ultrasonication" or equally "sonication" is a commonly used laboratory-scale method to disrupt cells. This method uses high frequency sound waves to cause cavitations within the fluid.

Indeed the present invention provides for SEDDS comprising CBD, THC, and related *Cannabis* preparations comprising higher efficiencies than with typical hydrophobic API, resulting in mixtures capable of higher bioavailability, as is further described in the below examples.

EXAMPLES

The below examples set forth non-limiting embodiments, and for each example SEDDS preparations may be varied for suitable administration means known by those skilled in the art.

Example 1—Particle Size Analysis of Micelles

A fully suspended mixture of CBD (0.01% w/w total), ethanol (0.01% w/w total), sorbitan trioleate (0.016% w/w total), and polysorbate 80 (0.0002% w/w total) was prepared in water (99.91% w/w total) with disodium ethylenediaminetetraacetic acid (0.05% w/w total) as a preservative. The solution is ultrasonicated to reduce the micelle particle sizes within the formulation. The remaining emulsion (pH=7.1) is stable for several days at room temperature but can be shaken to form a stable emulsion if separated after prolonged storage. High sheer homogenization and ultrasonication are common methods to reduce oil droplet size and increase stability of micelle preparations. Furthermore, centrifugation can be used to separate the micelle encapsulated CBD from the oil phase pellet. The pellet containing non-encapsulated CBD can be resuspended in water, mixed, and sonicated to obtain further micelle encapsulated CBD. This step can be repeated and the aqueous fractions combined and concentrated by vacuum lyophilization. Alternatively, the emulsion can be filtered through various membranes and porosities to obtain only the encapsulated micelles or methods known by other methods known by those skilled in the art to obtain pure, encapsulated cannabinoid micelles.

Figure 1:
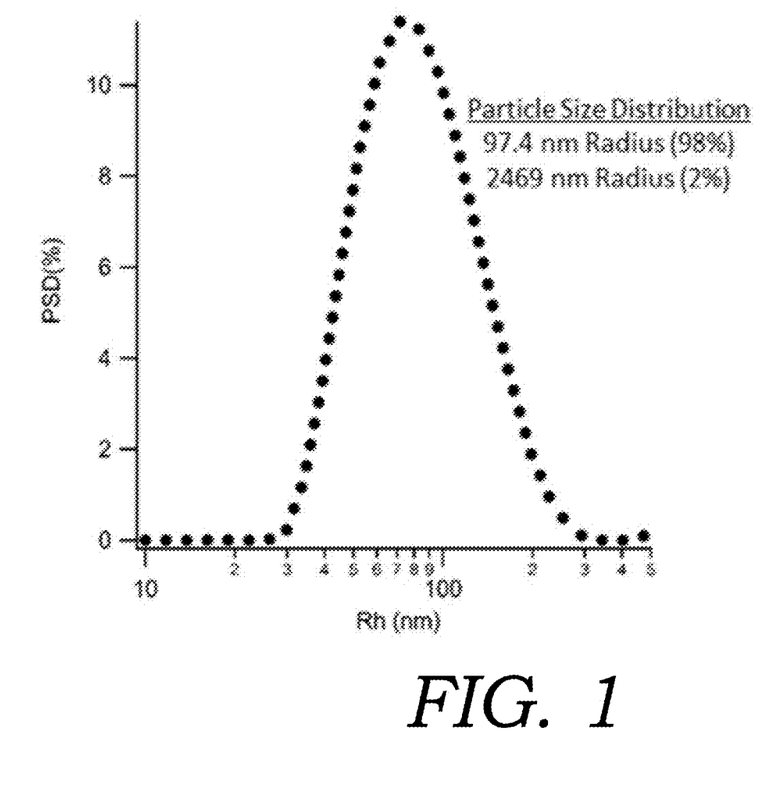
FIG. 1 depicts particle size distribution of micelles created in one emulsified formulation (Example 1).

Dynamic light scattering (DLS) is a technique to determine the hydrodynamic diameter of micelles using the Brownian and Stokes-Einstein equations. A Malvern Zetasizer was used to determine the size of formed micelle particles. Two distinct sizes were observed but the micelle diameter of 194.8 nm was strongly preferred, while only 2% of the micelles were a result of larger drug agglomerates (FIG. 1).

Example 2. Oral Suspension Formulation

In an exemplary embodiment, pharmaceutical ingredients are encapsulated using an emulsion-type formulation creating small particles with increased bioavailability constituting a novel cannabinoid delivery system. Cannabinoids can include but are not limited to cannabidiol, Δ9-tetrahydrocannabidiol, cannabinol, and respective acidic forms. Table 1 presents the exemplary formulation of the present invention.

TABLE 1

| Formulation of oral suspension (tincture) | |
|---|---|
| Ingredient | Concentration (Weight %) |
| Vegetable Glycerin | 53.1 |
| Ethyl Alcohol (EtOH) | 27.0 |
| Medium Chain Triglycerides (MCT Oil) | 9.96 |
| Water (H$_2$O) | 3.61 |
| Sunflower Oil | 2.89 |
| Oleic Acid | 2.44 |
| Cannabidiol (CBD) | 1.00 |
| *Quillaja saponaria* | 0.11 |

Example 3. Formulation of Oral Suspension Using *Aloe vera* and *Q. saponaria*

Table 2 presents an alternative embodiment of the present invention.

TABLE 2

Cannabinoid composition and concentrations (w/w).

| Ingredient | Concentration (Weight %) |
|---|---|
| Vegetable Glycerin | 49.9 |
| Ethyl Alcohol (EtOH) | 27.1 |
| Medium Chain Triglycerides (MCT Oil) | 10.1 |
| Water (H$_2$O) | 3.65 |
| Sunflower Oil | 2.82 |
| Oleic Acid | 2.34 |
| RSO Full Spectrum Extract | 1.00 |
| *Aloe vera* | 2.93 |
| *Quillaja saponaria* | 0.12 |

All ingredients are listed as a weight percentage in the formulation, and batch size may vary as needed. Oral suspensions in the form of emulsions tend to separate over time (approximately 1-2 weeks for the current invention). The solution may be shaken (by hand, sonication, or by other mechanical means) to return the solution back into its suspended form. The mixture can be stored at 4° C. to reduce settling, in an amber or other light-omitting container to reduce UV degradation of active ingredients. All glassware and mixing apparatuses must be pre-cleaned via soap and water, rinsing with isopropyl alcohol, or ethanol. In addition, mixing should be done under aseptic conditions to ensure a sterile product.

The methods set forth herein make an oil-in-water emulsion in which the cannabinoid is encapsulated by the surfactants (MCT, oleic acid, sunflower oil, *Q. saponaria* extract); this creates micelles of small particle sizes and greatly increases the water solvation properties. The composition of the present invention does not include any phospholipid technologies previously published (i.e. lecithin or phosphatidylcholine) instead using nonionic surfactants known in the art. Micelle formation is predicted to originate from the saponins present in *Q. saponaria* in addition to the other surfactants used in the oil phase component. The increased solubility leads to greater oral mucosal and gastrointestinal absorption and overall bioavailability requiring lower concentrations of the active ingredients per effective dose.

Figure 2:
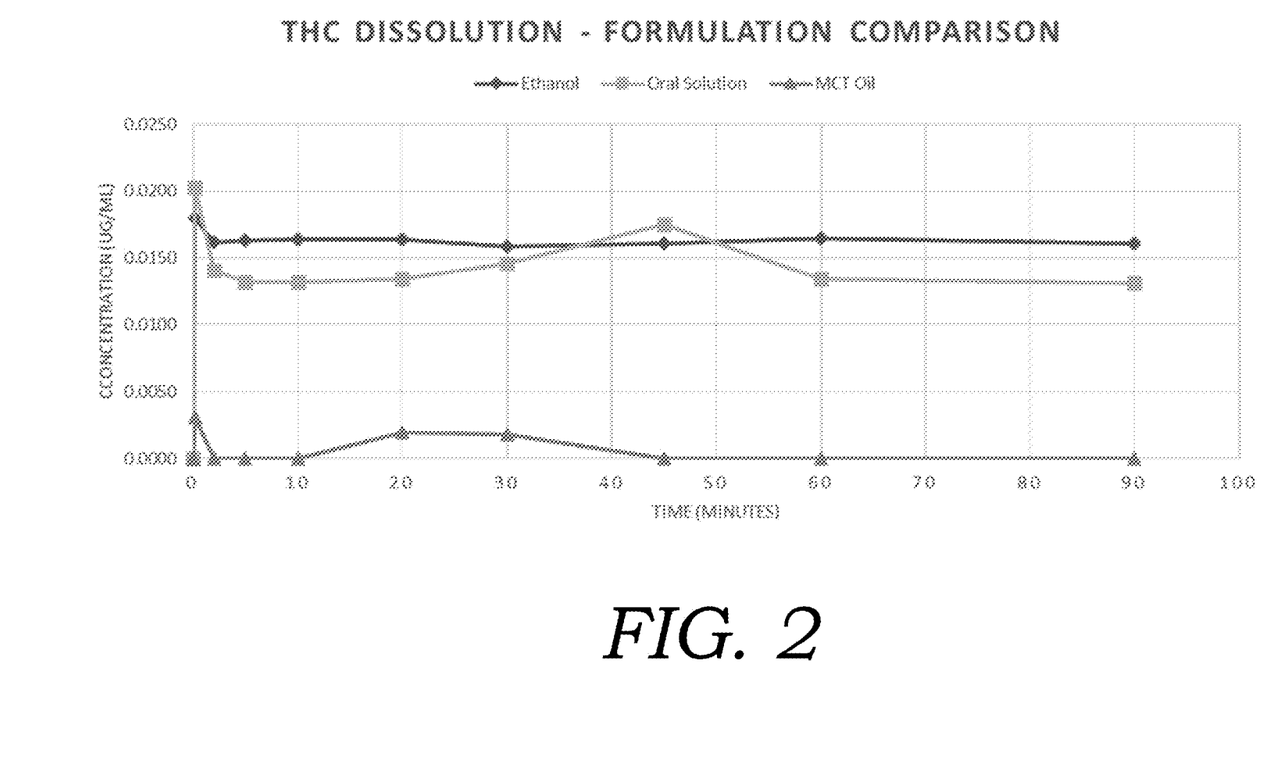
FIG. 2 depicts a graph showing dissolution profiles of each THC oral formulation (ethanol, oral formulation of the present invention (oral solution), and MCT Oil).

In order to show solubility in water, dissolution of the aforementioned oral oil-in-water (o/w) emulsion containing 1% w/w Δ19-tetrahydrocannabidiol (THC) was assessed over 90 minutes (see FIG. 2). This was then compared to two equivalent formulations using ethanol only and MCT oil only as the THC dissolving solutions. The dissolution was performed using 600 mL reservoirs filled with 500 mL of deionized (DI) water (see USP-40 Official Monograph page 3909 for dissolution of dronabinol capsules in sesame oil). Each container was held at a consistent physiologically relevant temperature of 37° C. with stir bars spinning at a constant 60 rpm.

Approximately 1 g of solution was added to each reservoir and 1 mL of the formulations in water were removed at each time point. Timepoints include a blank test of the DI water, an initial sample pull after addition, and 2 min, 5 min, 10 min, 20 min, 30 min, 45 min, 60 min, and 90 min. Each sample was directly injected onto a Waters H-Class UPLC for THC quantitation.

In order to show solubility in water and gut membrane permeation, the three aforementioned formulations were additionally tested for flux and permeability across a gastrointestinal tract (GIT) mimicking lipid membrane over 72 hours. This was performed using a Franz Cell Apparatus, and the three formulations included the o/w encapsulated oral solution (tincture) with 1% w/w THC, an equivalent potency ethanol only solution, and an MCT oil only solution (permeation was never observed). The lipid membrane consisted of a 47 mm, 0.2 μm Millipore PVDF membrane with approximately 50 mg of GIT-0 lipid membrane fluid provided by Pion Inc. Miniature stir bars were placed in the receiving reservoir of the Franz Cell Apparatus along with DI water held at a constant physiologically relevant temperature of 37° C. Using a positive displacement pipette, 1 mL of each formulation was placed into their individual donor cell on top of the membrane. Parafilm was used to cover the top of the donor cell to prevent excessive evaporation of any ethanol or similar solvents.

Sampling the donor cell was performed by removing 3 mL of fluid from the receiving cell and refilling with fresh DI water to the fill line. Timepoints include 5 min, 10 min, 15 min, 20 min, 30 min, 45 min, 60 min, 75 min, 90 min, 105 min, 120 min, 150 min, 180 min, 4 hr, 6 hr, 24 hr, 30 hr, 48 hr, 54 hr, and 72 hr. All sample pulls were directly injected onto a Waters H-Class UPLC for THC quantitation. MCT oil permeability is not shown, since THC was not detected in the receiving well at any time point during the 72-hour experiment.

Figure 3:
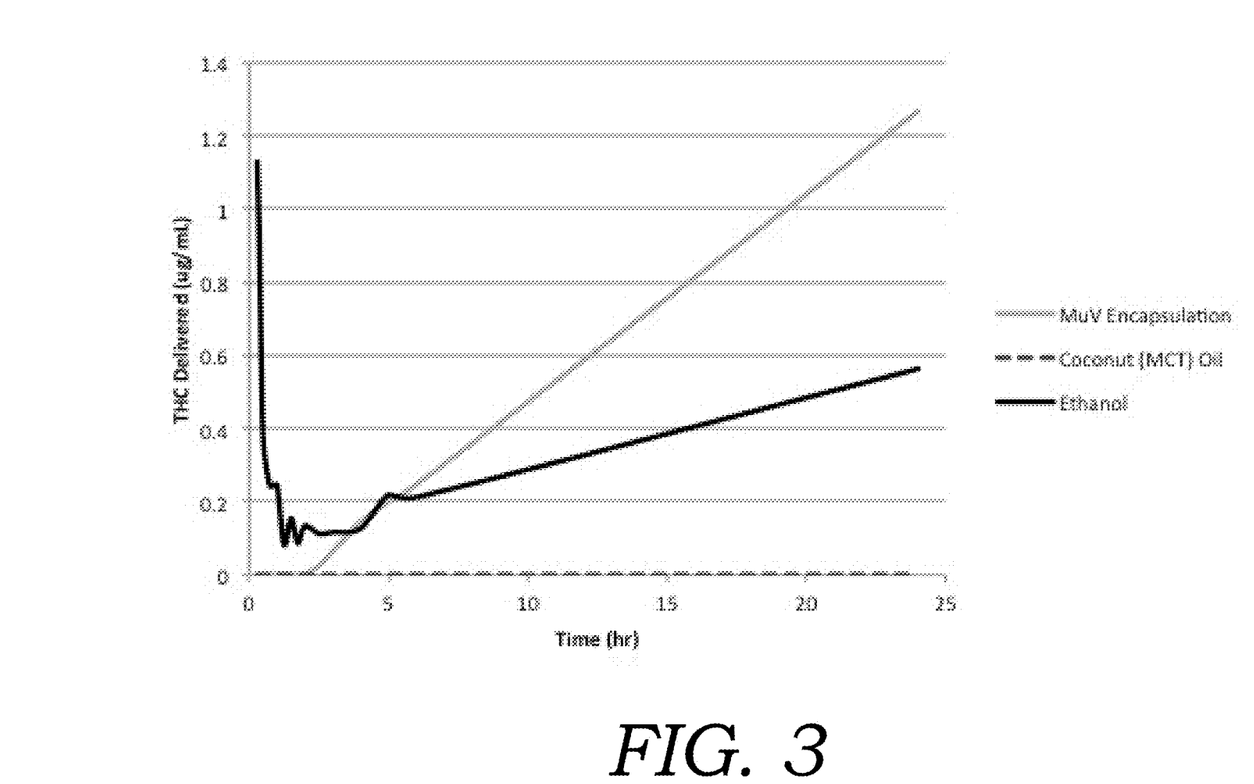
FIG. 3 depicts active ingredient (THC) delivery of an encapsulated oral composition having (1) the encapsulation of the present invention; (2) a coconut (MCT) oil-based composition, and (3) and ethanol composition.

Turning to FIG. 3, the permeability profile of the exemplary oil-in-water emulsion shows a gradual release of drug across the membrane over 25 hours whereas the ethanol solution was instantly released within the first 20 minutes. As mentioned previously, the MCT oil solution did not facilitate any THC membrane permeation. After completion of the exemplary embodiment, each PVDF membrane was analyzed for THC content trapped in the membrane. The ethanol solution contained the most trapped THC with 63.4 μg/mL of membrane-bound THC, the o/w emulsion and MCT oil solutions were comparable at 48 and 44 μg/mL of THC respectively. It is therefore presented that encapsulated THC oil-in-water (o/w) emulsion described herein shows solubility in water equivalent of pure ethanol solutions with a more desirable permeability profile across the GIT lipid membrane. As expected, solutions of THC (and other cannabinoids of similar polarity) dissolved in only MCT or similar oils (i.e. coconut oil, almond oil, olive oil, etc.) show no water solubility nor permeability across the GIT equivalent membrane providing zero protection throughout an environment such as the human body. The encapsulated formulation facilitates cannabinoid solubility and permeability therefore increasing bioavailability without the undesirable effects of a pure ethanol tincture.

Example 4—*Cannabis* Formulation for Oral, Sublingual, or Buccal Delivery

*Cannabis* extract (1% w/w total), ethanol (30% w/w total), oleic acid (5% w/w total), and medium chain triglycerides (5% w/w total) is prepared. Water (19% w/w total) and vegetable glycerin (40% w/w total) are added and high sheer mixed and sonicated to produce a translucent and stable emulsion. Then a stabilizer is added (Carbopol 974, 0.1% w/w total or *Quillaja* extract 0.2% w/w total) to further stabilize the syrup. Carbopol 974, an acrylate-based polymer, needs to be neutralized with a suitable base (sodium hydroxide or triethanolamine) while liquid *Quillaja* does not. Additionally, flavoring or sweeteners can be added for taste and a preservative can be used to increase shelf life and reduce microbial growth.

Additional formulations for high-water and/or beverage compositions are set forth in Table 3 which provides the concentrations of the cannabinoid composition, and Table 4, which provides the relative compositions of certain ingredients when added to 250 mL of water (or an equivalent beverages).

TABLE 3

High water formulation of oral suspension.

| Ingredient | Concentration (Weight %) |
| --- | --- |
| Water ($H_2O$) | 58.8 |
| Ethyl Alcohol (EtOH) | 30.0 |
| Medium Chain Triglycerides (MCT Oil) | 5.01 |
| Oleic Acid | 5.01 |
| Cannabis Extract | 1.00 |
| Quillaja saponaria | 0.13 |

TABLE 4

Concentration of oral suspension (tincture) ingredients when 1 mL is added to 250 mL of water (or equivalent beverage option).

| Ingredient | Concentration (Weight %) |
| --- | --- |
| Vegetable Glycerin | 0.212 |
| Ethyl Alcohol (EtOH) | 0.110 |
| Medium Chain Triglycerides (MCT Oil) | 0.027 |
| Water ($H_2O$) | 99.61 |
| Sunflower Oil | 0.012 |
| Oleic Acid | 0.010 |
| Cannabis Extract | 0.010 |
| Flavoring (Natural Terpenes) | 0.003 |
| Quillaja saponaria | 0.003 |

Figure 4:
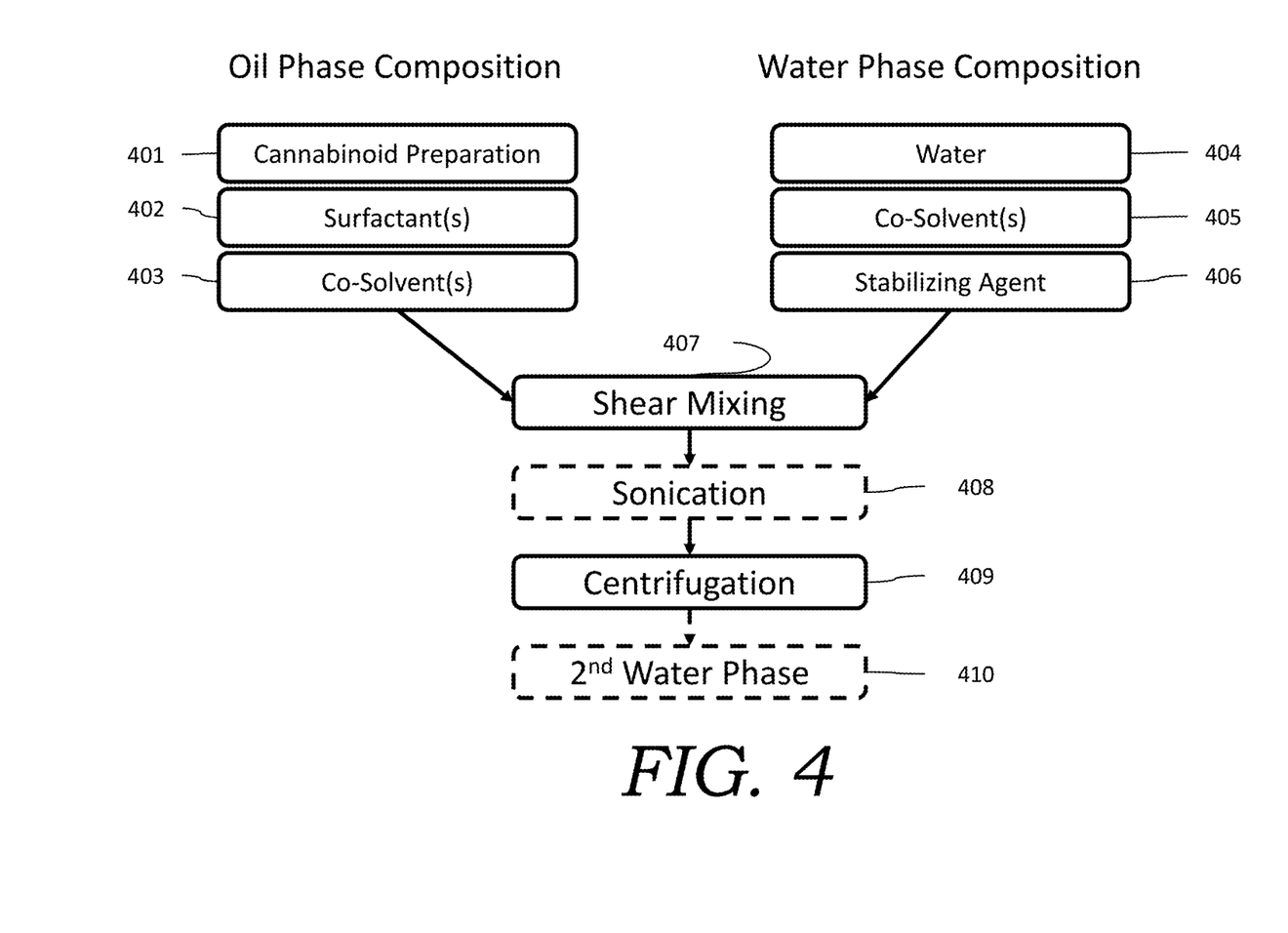
FIG. 4 depicts a flow diagram of the methods of the present invention.

The methods of the present invention are shown generally in FIG. 4, comprising and preparing oil phase composition comprising a cannabinoid preparation 401, one or more surfactants 402, and one or more co-solvents 403; preparing a water phase composition comprising water 404, one or more co-solvents 405, and one or more stabilizing agents 406. The oil phase composition and water phase composition are then subjected to shear mixing 407, followed by an optional sonication step 408 in order to reduce oil droplet size and increase stability of micelle preparations of the resulting mixed phases, followed by centrifugation 409 to separate the micelle encapsulated CBD from the oil phase pellet. Additional introduction of a second water phase composition 410 is then possible for purposes of obtaining further micelle encapsulated CBD, as previously noted. Additional optional shear mixing (not shown) or sonication step(s) 408 may be performed on beverages formulations.

Compositions of the present invention were analyzed for efficacy for various symptoms or conditions. 101 subjects responded to a survey following consumption of the compositions of the present invention wherein the cannabinoid ranged from (1) THC, (2) CBD, and (3) 50/50 THC/CBD. The average age was 58 and the median age was 61. 64% of survey respondents were female; 36% were male. In reference to pain relief, or chronic pain, there were 84 total responses: 71% effective; 24% neutral; 5% not effective. Approximately 50% of the 101 patients specifically use the claimed compositions for pain management (75% effective; 20% neutral; 5% not effective). For treating post-traumatic stress disorder (PTSD) and anxiety, there were 72 total responses: 71% effective; 24% neutral; 5% not effective. 27% of the 101 patients specifically use it for PTSD or anxiety (74% effective; 26% neutral; 0% not effective). For treatment of sleep related symptoms or disorders, such as insomnia, there were 78 total responses: 79% effective; 15% neutral; 6% not effective. 7% of the 101 patients specifically use it for Insomnia (100% effective). The remaining 16% of the 101 patients use the compositions of the present invention for cancer, epilepsy, gastrointestinal, multiple sclerosis, neurodegenerative diseases, and other immune disorders.

It is noted that the foregoing examples have been provided merely for the purpose of explanation and are in no way to be construed as limiting of the present invention. While the present invention has been described with reference to exemplary embodiments, it is understood that the words, which have been used herein, are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

REFERENCES

1. Griffin, William C. (1949), "Classification of Surface-Active Agents by 'HLB'", Journal of the Society of Cosmetic Chemists, 1 (5): 311-26
2. Chen J, Jian Q D, Chai Y P, Zhang H, Peng P, Yang X X. Natural terpenes as penetration enhancers for transdermal drug delivery. *Molecules*. 2016, 21, 1709.
3. Esposito E, Fantin L, Drechsler M, Mariani P, Contado C, Ruokolainen J, Ratano P, Campolngo P, Trezza V, Nastruzzi C, Cortesi R. Cannabinoid antagonist in nanostructured lipid carriers (NLC): design, characterization, and in vivo study. *Mater. Sci Eng.* 2015, 48, 328-336.
4. Hung O, Zamecnik J, Shek P N, Tikuisis P. Pulmonary delivery of liposome-encapsulated cannabinoids. International Patent No. 01/03668.
5. Keller B C, Fisher D L, Kiss S. Delivery of biologically active material in a liposomal formulation for administration into the mouth. U.S. Pat. No. 5,891,465.
6. Kwon, G S. Micelle encapsulation of therapeutic agents. U.S. patent application Ser. No. 12/668,269.
7. Lodzki M, Godin B, Rakou L, Mechoulam R, Gallily R, Touitou E. Cannabidiol-transdermal delivery and anti-inflammatory effect in a murine model. *J. Control. Release*. 2003, 93, 377-387.
8. Narang A S, Delmarre D, Gao D. Stable drug encapsulation in micelles and microemulsions. *Int. J. Pharm.* 2007, 345, 9-25.
9. O'Driscoll C M, Griffin B T. Biopharmaceutical challenges associated with with drugs with low aquous solubility—the potential impact of lipid-based formulations. *Adv. Drug Deliv. Rev.* 2008, 60, 617-624.
10. Smith N. Transdermal cannabinoid patch. US patent 2015/026316 filed Apr. 17, 2015.
11. Touitou E, Dayan N, Bergelson L, Godin B, Eliaz M. Ethosomes—novel vesicular carriers for enhanced delivery: characterization and skin penetration properties. *J. Control. Release*. 2000, 65, 403-418

What is claimed is:

1. A cannabinoid composition for oral delivery, said composition comprising:
   a cannabinoid preparation ranging from 0.001% to 3% (w/w);
   at least one surfactant ranging from 2% to 15% (w/w);
   at least one co-solvent ranging from 20% to 65% (w/w);
   at least one flavoring composition ranging from 0.1% to 5% (w/w);
   a preservative ranging from 0.01% to 5% (w/w); and
   water ranging from 2% to 77% (w/w);
wherein said preparation is encapsulated by surfactants to form micelles having uni-, bi-, or multi-lamellar structures and yields the cannabinoid preparation capable of having increased bioavailability and operable for oral delivery.

2. The cannabinoid composition of claim 1, wherein said composition is capable of oral, sublingual or buccal delivery.

3. The cannabinoid composition of claim 1, wherein the at least one surfactant comprises two or more surfactants.

4. The cannabinoid composition of claim 3, wherein the two or more surfactants comprise an HLB in the range of 1 to 8 and form a self-assembling emulsion.

5. The cannabinoid composition of claim 1, wherein the at least one surfactant comprises an HLB in the range of 9-20.

6. The cannabinoid composition of claim 1, wherein the at least one surfactant is selected from a group consisting of: oleic acid, sunflower oil, lecithin, phosphatidylcholine, isopropyl myristate, stearic acid, medium and long chain triglycerides (including Labrasol), polysorbate 20, polysorbate 80, or other ethoxylated surfactant, and sorbitan trioleate, other sorbitan surfactant, or combinations thereof.

7. The cannabinoid composition of claim 1, wherein the at least one co-solvent is selected from a group consisting of: methanol, ethanol, isopropyl alcohol, butanol, pentanol, hexanol, ethylene glycol, glycerin, propylene glycol, dipropylene glycol, glycerol, erythritol, xylitol, mannitol, sorbitol, diethylene glycol monoethyl ether (Transcutol), any derivative thereof, and combinations relating thereto.

8. The cannabinoid composition of claim 1, further comprising a stabilizer in the range of 0.01% to 3% (w/w).

9. The cannabinoid composition of claim 1, further comprising a thickening agent in the range of 0.01% to 10% (w/w).

10. The cannabinoid composition of claim 1, further comprising terpenes in the range of 0.1% to 5% (w/w).

11. A cannabinoid composition for consumption as a beverage, said composition comprising:
   a first measured amount of a cannabinoid-containing suspension comprising:
      a cannabinoid preparation ranging from 0.001% to 3% (w/w);
      at least one surfactant ranging from 2% to 15% (w/w);
      at least one co-solvent ranging from 20% to 65% (w/w);
      at least one flavoring composition ranging from 0.1% to 5% (w/w);
      a preservative ranging from 0.01% to 5% (w/w); and
      water ranging from 2% to 77% (w/w); and
   a liquid composition;
wherein said cannabinoid preparation is encapsulated by surfactants to form micelles having uni-, bi-, or multi-lamellar structures and yields the cannabinoid-containing suspension preparation capable of having increased bioavailability when consumed as a beverage.

12. The cannabinoid composition of claim 11, wherein the at least one surfactant comprises two or more surfactants.

13. The cannabinoid composition of claim 12, wherein the two or more surfactants comprise an HLB in the range of 1 to 8 and form a self-assembling emulsion.

14. The cannabinoid composition of claim 11, wherein the at least one surfactant comprises an HLB in the range of 9-20.

15. The cannabinoid composition of claim 11, wherein the at least one surfactant is selected from a group consisting of: oleic acid, sunflower oil, lecithin, phosphatidylcholine, isopropyl myristate, stearic acid, medium and long chain triglycerides (including Labrasol), polysorbate 20, polysorbate 80, or other ethoxylated surfactant, and sorbitan trioleate, other sorbitan surfactant, or combinations thereof.

16. The cannabinoid composition of claim 11, wherein the at least one co-solvent is selected from a group consisting of: methanol, ethanol, isopropyl alcohol, butanol, pentanol, hexanol, ethylene glycol, propylene glycol, dipropylene glycol, glycerol, glycerin, erythritol, xylitol, mannitol, sorbitol, diethylene glycol monoethyl ether (Transcutol), any derivative thereof, and combinations relating thereto.

17. The cannabinoid composition of claim 11, further comprising a stabilizer in the range of 0.01% to 3% (w/w).

18. The cannabinoid composition of claim 11, further comprising a thickening agent in the range of 0.01% to 10% (w/w).

19. The cannabinoid composition of claim 11, further comprising terpenes in the range of 0.1% to 5% (w/w).

* * * * *